(12) United States Patent
Gray et al.

(10) Patent No.: US 7,915,435 B2
(45) Date of Patent: *Mar. 29, 2011

(54) ALKYL-CAPPED ALKOXYLATED ESTERS AND COMPOSITIONS COMPRISING SAME

(75) Inventors: Lon Montgomery Gray, Florence, KY (US); Jeffrey John Scheibel, Loveland, OH (US); Phillip Kyle Vinson, Fairfield, OH (US); Christopher James Binski, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/391,162

(22) Filed: Mar. 28, 2006

(65) Prior Publication Data

US 2006/0167293 A1    Jul. 27, 2006

Related U.S. Application Data

(62) Division of application No. 10/990,790, filed on Nov. 17, 2004, now Pat. No. 7,081,541, and a division of application No. 10/319,935, filed on Dec. 16, 2002, now Pat. No. 6,849,751.

(60) Provisional application No. 60/342,724, filed on Dec. 20, 2001.

(51) Int. Cl.
*A23D 9/00* (2006.01)

(52) U.S. Cl. .................................................... 554/227
(58) Field of Classification Search ................. 554/227
See application file for complete search history.

(56) References Cited

U.S. PATENT DOCUMENTS

| 1,970,578 | A | 8/1934 | Schoeller et al. |
| 3,539,518 | A | 11/1970 | Feighner et al. |
| 3,865,803 | A | 2/1975 | Falkehag |
| 4,739,040 | A | 4/1988 | Naae et al. |
| 5,817,844 | A | 10/1998 | Hama et al. |
| 5,972,047 | A | 10/1999 | Dilling et al. |
| 6,100,385 | A | 8/2000 | Naae et al. |
| 6,184,400 | B1 | 2/2001 | Hama et al. |

FOREIGN PATENT DOCUMENTS

| CH | 232 099 A | 5/1944 |
| EP | 0 899 872 B1 | 3/1997 |
| FR | 906 335 A | 12/1945 |
| WO | WO 89/06684 A | 7/1989 |

OTHER PUBLICATIONS

U.S. Appl. No. 11/390,905, filed Mar. 28, 2006, Gray et al.
U.S. Appl. No. 11/391,154, filed Mar. 28, 2006, Gray et al.
U.S. Appl. No. 11/391,158, filed Mar. 28, 2006, Gray et al.

*Primary Examiner* — James O Wilson
*Assistant Examiner* — Jeffrey H Murray
(74) *Attorney, Agent, or Firm* — Stephen T. Murphy

(57) ABSTRACT

Process of making alkyl-capped alkoxylated esters. More specifically, a process of making alkyl-capped alkoxylated esters that are comprised substantially of triethylene alkoxy ester and substantially free from ethylene glycol monoalkoxy monoester and diethylene glycol monoalkoxy monoester.

1 Claim, 2 Drawing Sheets

ALKYL-CAPPED ALKOXYLATED ESTERS AND COMPOSITIONS COMPRISING SAME

CROSS REFERENCE TO RELATED APPLICATIONS

This application is a divisional application of U.S. Ser. No. 10/990,790, filed Nov. 17, 2004 now U.S. Pat. No. 7,081,541; and U.S. Ser. No. 10/319,935, filed Dec. 16, 2002 now U.S. Pat. No. 6,849,751; which claims priority under 37 U.S.C. §119(e) to U.S. Provisional Application Ser. No. 60/342,724, filed Dec. 20, 2001.

FIELD OF THE INVENTION

The present invention relates to alkyl-capped alkoxylated esters and a process of making the same. The compounds of the present invention comprised substantially of an alkyl-capped alkoxylated ester having formula (I).

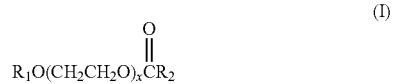

wherein x being equal to or greater than 3; with the alkyl-capped alkoxylated esters being substantially free from ethylene glycol monoalkoxy monoester having the formula (I), wherein x is equal to 1 and diethylene glycol monoalkoxy monoester having the formula (I), wherein x is equal to 2, to provide a meaningful alternative to conventional ethoxylates, some of which have been associated with higher toxicity and higher sudsing. When incorporated into a cleaning or detergent composition in accordance with the present invention, the claimed alkyl-capped alkoxylated esters exhibit enhanced cleaning performance and lower toxicity, particularly in comparison to conventional ethoxylates.

BACKGROUND OF THE INVENTION

There exists a plethora of surfactants in the detergency art. Surfactants, which are comprised of both a hydrophilic and a hydrophobic segment, serve the integral purpose of reducing the surface tension of the substrate to which they are applied. Surfactants are particularly useful for purposes of wetting, emulsifying, dispersing, foaming, scouring and/or lubricity. Indeed, alcohol ethoxylates (AEs) are common surfactants that are employed often for their detergency and emulsification properties.

With the promulgation of recent regulations and initiatives directed at the reduction of nonylphenol ethoxylates (NPEs), some of which have been associated with biodegradation and toxicity issues, other ethoxylates have become primary alternatives to those skilled in the art. Nevertheless, a few conventional ethoxylated surfactants, too, have been linked to adverse affects on the environment. In particular, certain ethoxylates characterized by high levels of ethylene glycol monoalkoxy mono ester, diethylene glycol monoalkoxy monoester, ethylene glycol alkyl ether, $R_1O(CH_2CH_2O)_nH$, wherein n is equal to 1 and diethylene glycol alkyl ether, $R_1O(CH_2CH_2O)_nH$, wherein n is equal to 2, have been identified.

It is predicted that the use of these ethoxylates will substantially decline and will likely result in a deficiency of meaningful alternatives to conventional surfactants, and particularly the widely employed nonylphenol ethoxylates.

Thus, there exists a substantial need in the surfactant and detergency arts to identify and deploy meaningful and environmentally friendly alternatives to conventional ethoxylates, and specifically alcohol ethoxylates, methyl ester ethoxylates, and nonylphenol ethoxylates. Any meaningful enhancement upon said conventional ethoxylates should deliver the benefits of high performance and the reduction of negative attributes. Furthermore, any meaningful improvement upon conventional ethoxylates should likely convey the benefit of enhanced biodegradation.

The alkyl-capped alkoxylated esters of the present invention address the problems associated with conventional ethoxylates, and specifically alcohol ethoxylates, methyl ester ethoxylates and nonylphenol ethoxylates, as will become apparent from the following disclosure.

SUMMARY OF THE INVENTION

The present invention addresses problems associated with conventional ethoxylates, and specifically alcohol ethoxylates, methyl ester ethoxylates and nonylphenol ethoxylates. Indeed, the alkyl-capped alkoxylated ester compounds (hereinafter "ACAEs") of the present invention are characterized by high performance and reduction of negative attributes, particularly in comparison to conventional ethoxylates. Moreover, the compounds of the present invention experience enhanced biodegradation. An embodiment of the present invention is an alkyl-capped alkoxylated ester having the formula (I):

wherein $R_1$ is a $C_1$ to $C_4$ hydrocarbon, linear or branched, and mixtures thereof, $R_2$ is $C_7$ to $C_{22}$ hydrocarbon, linear or branched, and mixtures thereof; and x is equal to or greater than 3; such that the alkyl-capped alkoxylated ester is substantially free of ethylene glycol monoalkoxy monoester having formula (I) wherein x is equal to 1 and diethylene glycol monoalkoxy monoester having formula (I) wherein x is equal to 2, and is substantially free of ethylene glycol alkyl ether ($R_1O(CH_2CH_2O)H$ unit) and diethylene glycol alkyl ether ($R_1O(CH_2CH_2O)_2H$ unit).

Another embodiment of the present invention is the process of preparing an alkyl-capped alkoxylated ester, having the formula (I).

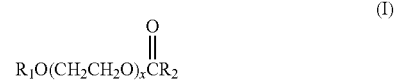

wherein $R_1$ is a $C_1$ to $C_4$ hydrocarbon, linear or branched, and mixtures thereof, $R_2$ is $C_7$ to $C_{22}$ hydrocarbon, linear or branched, and mixtures thereof; and x is equal to or greater than 3. The claimed process comprises the steps of ethoxylating a compound having the structural formula: $R_1O(CH_2CH_2O)_nH$ wherein $R_1$ is defined as above and the index of n is greater than or equal to 3; wherein said compound, $R_1O(CH_2CH_2O)_nH$, is comprised substantially of ethylene glycol alkyl ethers, $R_1O(CH_2CH_2O)_nH$, wherein n is equal to or greater than 3, and is substantially free of ethylene glycol alkyl ether, $R_1O(CH_2CH_2O)H$ unit, wherein n of the ethylene glycol alkyl ethers formula is equal to 1; and diethylene glycol alkyl ether, $R_1O(CH_2CH_2O)_2H$ unit, wherein n of the ethylene glycol alkyl ethers formula is equal to 2; by reacting said compound with an ethoxylating agent having the formula (II):

(II)

and conducting the ethoxylation step in the presence of a base; defined herein below, reacting the product of said ethoxylation step with formula (III):

(III)

wherein $R_2$ is as defined above in formula (I) and $R_3$ is a $C_1$ to $C_4$ hydrocarbon, linear or branched, and mixtures thereof; wherein said reaction in the presence of a base catalyst, defined herein below; heating to a temperature of from about 60° C. to about 200° C.; and optionally, at a pressure from about 20 kPa to about 0.013 kPa (200 mm Hg to 0.1 mm Hg) for 0.1 to 10 hours.

An embodiment of the present invention comprises another process for preparing the ACAEs, having the formula (I). The process comprises the steps of: stripping substantially a conventional polyethylene glycol alkyl ethers of ethylene glycol alkyl ether ($R_1O(CH_2CH_2O)H$ unit) and diethylene glycol alkyl ether ($R_1O(CH_2CH_2O)_2H$ unit); reacting the stripped product with a compound having the formula (III) in the presence of a base catalyst, defined herein below, heating to a temperature of from about 60° C. to about 200° C., optionally, at a pressure ranging from about 20 kPa and about 0.013 kPa (200 mm Hg to 0.1 mm Hg) for 0.1 to 10 hours, and optionally, recycling said ethylene glycol alkyl ether ($R_1O(CH_2CH_2O)H$ unit) and diethylene glycol alkyl ether ($R_1O(CH_2CH_2O)_2H$ unit) from the first step of said reaction.

Another embodiment of the present invention incorporates the ACAEs into cleaning compositions.

These and other objects, features, and advantages will become apparent to those of ordinary skill in the art from a reading of the following detailed description and the appended claims. All percentages, ratios and proportions herein are by weight of a cleaning composition unless otherwise specified. All temperatures are in degrees Celsius (° C.) unless otherwise specified. All documents cited are in relevant part, incorporated herein by reference.

DETAILED DESCRIPTION OF THE INVENTION

Figure 1:
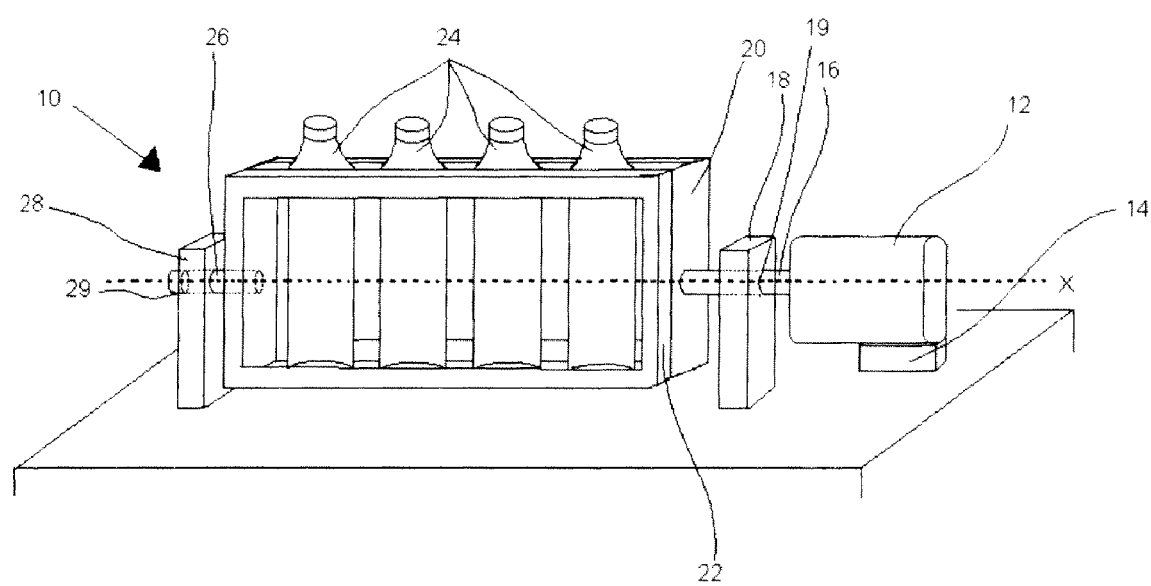
FIG. 1 is a mixing apparatus for measuring suds volume.

The alkyl-capped alkoxylated esters of the present invention are substantially free of conventional ethylene glycol monoalkoxy monoester having the formula (I).

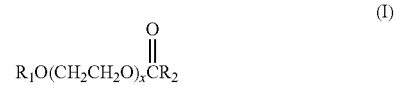
(I)

wherein x is equal to 1, herein after referred to as "$R_1E_1$" constituents and diethylene glycol monoalkoxy monoester having the formula (I) wherein x is equal to 2, herein after referred to as "$R_1E_2$" constituents. Additionally, the alkyl-capped alkoxylated esters of the present invention are substantially free of ethylene glycol alkyl ether ($R_1O(CH_2CH_2O)H$ unit) and diethylene glycol alkyl ether ($R_1O(CH_2CH_2O)_2H$ unit). "Substantially free" is defined herein to mean that $R_1E_1$ and $R_1E_2$ constituents and the $R_1O(CH_2CH_2O)H$ unit and $R_1O(CH_2CH_2O)_2H$ unit comprise less than 5% by weight of the alkyl-capped alkoxylated esters, preferably from about 1% to 0% by weight of the alkyl-capped alkoxylated esters. Conversely, "substantially free" means that the resulting alkyl-capped alkoxylated esters comprises from about 95% to about 100%, preferably about 99% to about 100% of a constituent of formula (I) wherein x is equal to or greater than 3.

As used herein "conventional ethoxylates" include but are not limited to alcohol ethoxylates, methyl ester ethoxylates, and nonylphenol ethoxylates. As used herein "cleaning compositions" include, but are not limited to household cleaning compositions such as hard surface cleaners (i.e., floor cleaners, glass cleaners) granular laundry detergents, liquid laundry detergents, toilet cleaners, car cleaners, carpet cleaners, appliance cleaners, wall cleaners and non-aqueous based cleaning systems, including many of the newer systems which are based on silicones, ethers or carbon dioxide, inter alia.

Alkyl-Capped Alkoxylated Ester Compounds (ACAE)

The alkyl-capped alkoxylated ester compounds ("ACAE") of the present embodiment is illustrated by formula (I):

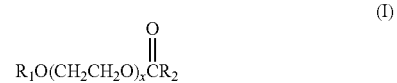
(I)

wherein $R_1$ is a $C_1$ to $C_4$ hydrocarbon, linear or branched, and mixtures thereof, $R_2$ is $C_7$ to $C_{22}$ hydrocarbon, linear or branched and mixtures thereof and the index of x is equal to or greater than 3. The ACAEs of the present invention provide a meaningful and viable alternative to conventional ethoxylates, such as $R_1E_1$ and $R_1E_2$, alcohol ethoxylates, methyl ester ethoxylates and nonylphenol ethoxylates.

Process

In accordance with the present invention, a process for preparing the ACAEs of the claimed invention, is disclosed. Thus, the present embodiment relates to a preferred process of preparing the ACAEs discussed above having the formula (I).

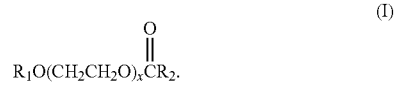
(I)

wherein $R_1$ is a $C_1$ to $C_4$ hydrocarbon, linear or branched, and mixtures thereof, $R_2$ is $C_7$ to $C_{22}$ hydrocarbon, linear or branched and mixtures thereof and the index of x is equal to or greater than 3. The claimed process comprises the steps of ethoxylating a starting material having formula $R_1O(CH_2CH_2O)_nH$; wherein $R_1$ is as defined above in formula (I) and the index of n is greater than or equal to 3; wherein said starting material is substantially free of ethylene glycol alkyl ether ($R_1O(CH_2CH_2O)H$ unit) and diethylene glycol alkyl ether ($R_1O(CH_2CH_2O)_2H$ unit), and reacting said starting material with an ethoxylating agent having the formula (II):

(II)

conducting the ethoxylation step in the presence of a base, discussed below; to form a product of said ethoxylation. Next, reacting the product of said ethoxylation with a compound having the formula (III):

(III)

wherein $R_2$ is defined as above for formula (I) and $R_3$ is a $C_1$ to $C_4$ linear or branched hydrocarbon or mixtures thereof; conducting said reaction in the presence of a base catalyst, discussed below; applying heat to said reaction, ranging in temperature of from about 60° C. to about 200° C.; and optionally, conducting said all or part of said process in a vacuum ranging from about 20 kPa to about 0.013 kPa (200 mm Hg to 0.1 mm Hg), preferably about 3.33 kPa to about 0.133 kPa (25 mm to 1 mm Hg), for a period of time ranging from 0.1 to 10 hours to form the ACAEs of the present invention.

The base used for ethoxylation can be any of the conventional bases known in the art. Non-limiting examples such as NaOH, Na metal, KOH, $Mg(OH)_2$, $Ca(OH)_2$, Rare earth alkoxides, are all of bases which may be used for the ethoxylation. Additionally, acceptable bases include, but are not limited to, conventional and narrow range alkoxylation catalysts. Although not preferred acidic ethoxylation catalysts such as $BF_3$ and others reported in the art may be used.

The base catalysts may be the same as the base described above for the ethoxylation step or may differ from the base used for the ethoxylation step. Indeed, the practitioner of the invention may choose not to add any additional base catalyst if the base from the ethoxylation step is not neutralized, since the base from the ethoxylation step should be sufficient in acting additionally as the base catalyst to carry out the second step of said process to prepare the ACAE's of the present invention.

Thus, in accordance with another preferred embodiment of the present invention, an alternative process with which to generate the ACAEs of the present invention is disclosed. The ACAEs of the present invention are illustrated by the following chemical structure in formula (I):

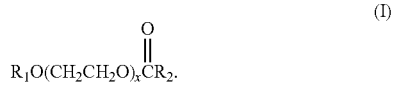
(I)

wherein $R_1$ is a $C_1$ to $C_4$ hydrocarbon, linear or branched, and mixtures thereof, $R_2$ is $C_7$ to $C_{22}$ hydrocarbon, linear or branched, and mixtures thereof, and the index of x is greater than or equal to 3. The process of yielding the compound of formula (I) comprises the steps of stripping substantially a conventional polyethylene glycol alkyl ether of ethylene glycol alkyl ether ($R_1O(CH_2CH_2O)H$ unit) and diethylene glycol alkyl ether ($R_1O(CH_2CH_2O)_2H$ unit), reacting the stripped product with a compound having the formula (III):

(III)

wherein $R_2$ is as defined in formula (I) above and $R_3$ is $C_1$ to $C_4$ hydrocarbon, linear or branched, and mixtures thereof; and conducting said reaction in the presence of a base, applying heat to said reaction, ranging in temperature of from about 60° C. to about 200° C., optionally, conducting all or part of said reaction in a vacuum ranging from about 20 kPa to about 0.013 kPa (200 mm Hg to 0.1 mm Hg), preferably about 3.33 kPa to about 0.133 kPa (25 mm Hg to 1 mm Hg), for a period of time ranging from 0.1 to 10 hours to form the ACAEs of the present invention, and optionally, recovering any $R_1O(CH_2CH_2O)H$ unit and $R_1O(CH_2CH_2O)_2H$ unit from the first step of said reaction;

The recovered $R_1O(CH_2CH_2O)H$ unit and $R_1O(CH_2CH_2O)_2H$ unit from the first step of said reaction may optionally be used to prepare additional conventional polyethylene glycol alkyl ether for use in said process, thus making the process more economical.

The stripping of the conventional polyethylene glycol alkyl ether constitutes a fundamental step in the above-described process embodiment. As used herein "stripping substantially" is defined as having the conventional polyethylene glycol alkyl ether, upon being stripped, possesses from about 95% to about 100%, preferably 99% to 100%, of $R_1O(CH_2CH_2O)_nH$, units wherein n is equal to or greater than 3. The term "stripping substantially" may also be defined on the basis of the $R_1O(CH_2CH_2O)H$ unit and $R_1O(CH_2CH_2O)_2H$ unit content of the stripped, polyethylene glycol alkyl ether of the present process embodiment. Upon stripping, said polyethylene glycol alkyl ether possesses from about 5% to about 0%, preferably 1% to 0%, of $R_1O(CH_2CH_2O)H$ unit and $R_1O(CH_2CH_2O)_2H$ unit. To reiterate, it is believed that the stripping step of the process of the present embodiment ensures that the resultant, ACAEs are substantially free from $R_1E_1$ and/or $R_1E_2$ constituents as well as any remaining unreacted $R_1O(CH_2CH_2O)H$ and/or $R_1O(CH_2CH_2O)_2H$ units, and is thereby characterized by low toxicity and low sudsing, particularly in comparison to conventional ethoxylates.

Indeed, said stripping may be achieved a variety of ways. Nonlimiting examples of preferred laboratory procedures that may be performed to strip the polyethylene glycol alkyl ethers of the present process include: distillation, vacuum distillation, thin film evaporation and combinations thereof. In a preferred embodiment of the present invention, said stripping may be conducted as an initial step of said process. In yet another preferred embodiment of the present invention, said stripping may be conducted as a final step of said process. To reiterate, the different process embodiments of the present invention are intended to serve different means with which to yield the ACAEs of the present invention. Some who practice the present invention may discover that the process of stripping the $R_1O(CH_2CH_2O)H$ unit and $R_1O(CH_2CH_2O)_2H$ unit from commercially available, conventional polyethylene glycol alkyl ether, presents an easier and/or less expensive means in which to generate the ACAEs of the present invention. Nevertheless, the selection of the appropriate process of the claimed invention is entirely within the discretion of the practitioner, as both processes are adapted to yield the ACAEs of the present invention.

Another embodiment of the present invention relates to a process of making the ACAEs having the formula (I):

$$R_1O(CH_2CH_2O)_xCR_2.$$  (I)

wherein $R_1$ is a $C_1$ hydrocarbon (methyl), linear or branched, and mixtures thereof, $R_2$ is $C_7$ to $C_{22}$ hydrocarbon, linear or branched, and mixtures thereof, and the index of x is greater than or equal to 3.

The claimed process comprises the steps of ethoxylating a starting material having formula $R_1O(CH_2CH_2O)_nH$; wherein $R_1$ is a $C_1$ hydrocarbon (methyl) and the index of n is greater than or equal to 3; wherein said starting material is substantially free of ethylene glycol alkyl ether ($R_1O(CH_2CH_2O)H$ unit) and diethylene glycol alkyl ether ($R_1O(CH_2CH_2O)_2H$ unit), and reacting said starting material with an ethoxylating agent having the formula (II):

  (II)

conducting the ethoxylation step in the presence of a base; reacting the product of said ethoxylation with a compound having the formula (III):

$$R_2COR_3$$  (III)

wherein $R_2$ is a $C_7$ to $C_{22}$ hydrocarbon, linear or branched, and mixtures thereof; and $R_3$ is a $C_1$ to $C_4$ linear or branched hydrocarbon or mixtures thereof; conducting said reaction in the presence of a base catalyst, applying heat to said reaction, ranging in temperature of from about 60° C. to about 200° C.; and optionally, conducting said all or part of said process in a vacuum ranging from about 20 kPa to about 0.013 kPa (200 mm Hg to 0.1 mm Hg), preferably about 3.33 kPa to about 0.133 kPa (25 mm to 1 mm Hg), for a period of time ranging from 0.1 to 10 hours to form a methyl fatty ester of formula (I).

The resulting methyl fatty ester of formula (I) is then reacted with ethylene oxide units via addition polymerization to form the ACAEs of the present invention. Preferably, the addition polymerization process utilizes a metal-oxide catalyst process described in U.S. Pat. No. 5,817,844 B1, Hama et al.; wherein the metal-oxide catalyst consists essentially of calcined aluminum magnesium hydroxide whose surface is modified with a metal hydroxide or a metal alkoxide. Additionally, a preferable additional polymerization process using suitable catalysts are discussed in EP 0 889 872 B1, which utilizes (a) alkali metal and/or alkaline earth metal hydroxides and/or alcoholates and (b) alkylene glycols as catalysts.

Product of Process

In yet another, preferred aspect of the present invention, the product of the aforementioned process is disclosed and claimed. The product yielded by performing the process of the present embodiment is illustrated by formula (I):

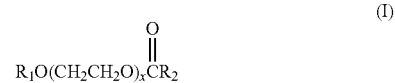  (I)

wherein $R_1$ is a $C_1$ to $C_4$ hydrocarbon, linear or branched, and mixtures thereof, $R_2$ is $C_7$ to $C_{22}$ hydrocarbon, linear or branched, and mixtures thereof, and the index of x is greater than or equal to 3; wherein the product yielded by performing the process of the present embodiment is substantially free from $R_1E_1$, $R_1E_2$, $R_1O(CH_2CH_2O)H$, and $R_1O(CH_2CH_2O)_2H$. Indeed, the ACAEs produced by performing the process of the present embodiment, provide a meaningful and viable alternative to conventional ethoxylates, and specifically alcohol ethoxylates, methyl ester ethoxylates and nonylphenol ethoxylates.

Without wishing to be bound by theory, it is believed that by conducting the ethoxylation step of the above process with an ethoxylate that is comprised substantially of an ethylene glycol alkyl ether ($R_1O(CH_2CH_2O)_nH$) wherein n is equal to or greater than 3, and substantially free of ethylene glycol alkyl ether ($R_1O(CH_2CH_2O)H$) and diethylene glycol alkyl ether ($R_1O(CH_2CH_2O)_2H$), the resultant ACAE is also substantially free from $R_1E_1$ and $R_1E_2$ constituents. The product of the process of the present embodiment is characterized by low toxicity, particularly in comparison to conventional ethoxylates, and specifically alcohol ethoxylates, methyl ester ethoxylates and nonylphenol ethoxylates. Moreover, the product of the present process comprises the additional benefit of low sudsing, particularly when compared to conventional ethoxylates. The low sudsing characteristics of the present compounds are particularly evident when the compounds are employed in a cleaning composition.

Cleaning Compositions

The ACAEs of the present invention yielded by performing the present process are substantially free from $R_1E_1$ and/or $R_1E_2$ constituents, and is substantially free of ethylene glycol alkyl ether ($R_1O(CH_2CH_2O)H$ unit) and diethylene glycol alkyl ether ($R_1O(CH_2CH_2O)_2H$ unit); and thereby characterized by low toxicity and low sudsing, particularly in comparison to conventional ethoxylates, and specifically alcohol ethoxylates, methyl ester ethoxylates and nonylphenol ethoxylates. The low sudsing characteristics of the ACAEs of the present invention are particularly evident when the ACAEs are employed in a cleaning composition. Thus, in accordance with another embodiment of the present invention is a cleaning composition comprising the novel, ACAEs of the present invention.

The use of the ACAEs of the present invention in cleaning compositions provide a meaningful and environmentally friendly alternative to the employment of conventional ethoxylates, specifically alcohol ethoxylates, methyl ester ethoxylates and nonylphenol ethoxylates, in a cleaning composition. The ACAEs of the present invention are characterized by several, performance benefits, particularly in comparison to conventional ethoxylates. Namely, the ACAEs of the present invention, and thus the cleaning compositions in which they are employed, experience low sudsing, and thus better overall detergency, in comparison to conventional ethoxylates, and specifically when compared with alcohol ethoxylates, methyl ester ethoxylates and nonylphenol ethoxylates.

Sudsing

Indeed, the low sudsing characteristics of the present invention are particularly evident when the ACAEs are employed in a cleaning composition. To illustrate the low sudsing benefits of the present ACAEs, a dilute detergent solution is prepared with de-ionized water such that the concentration of detergent is approximately 6000 ppm. This concentration is based on a dosage of 78 g of detergent in 13 L of water, which is typical for a horizontal axis machine wash process. A 100 mL aliquot of the dilute detergent solution is removed and carefully poured into a clean 1000 mL glass graduated cylinder. Just prior to mixing, enough concentrated hardness solution (9600 grains per gallon deionized water, 2 parts calcium, 1 part magnesium) is added to each cylinder to attain desired solution hardness and the cylinders are capped. A mixing apparatus, as shown in FIG. 1, rotates 4 cylinders simultaneously at a rate of 34 revolutions/minute. At selected time intervals of 2.5 minutes, the mixing is stopped and a visual reading of the suds volume is recorded. After mixing is completed, the cylinders are left uncapped and the suds volume is recorded at selected post-mixing time intervals of 2.5 minutes. The initial solution volume is subtracted from these readings to obtain the volume of suds produced.

Each test is performed in duplicate and an average value is reported. Needless to say, performance of the above procedure illustrates, unequivocally, the enhanced sudsing benefits of the claimed ACAEs of the present invention in comparison to conventional ethoxylates, and particularly alcohol ethoxylates.

FIG. 1 shows the mixing apparatus (10) used to measure the suds volume described above. The mixing apparatus (10) comprises an electrical motor (12), which is a Dayton Shaded Pole Gearmotor, model #3M158B, having 115 AC volts; 60 Hz, 2.5 Amps, 1/10 horsepower, 113 ln.lb in torque, and 30 F/L RPMs, that can be plugged into a power source. Attached to the underside of the motor (12) is a counter (14), which when wired to the motor indicates the number of rotations of the motor and the mixing apparatus (10). Affixed to and extending from the motor (10) is a crankshaft (16) that is rotated 360° by the motor (10). The motor (12) is mounted to a motor mount wall (18) being of sufficient thickness and width to support the motor (12) and sufficient height to allow the mixing apparatus (10) to rotate freely about axis X as shown in FIG. 1. The motor mount wall (18) comprises a motor mount wall opening (19), which the crankshaft (16) extends through and the motor mount wall opening (19) is of sufficient diameter to allow the crankshaft (16) to rotate freely about axis X. The crankshaft (16) is attached to and terminates at a piece of a main holding frame (20). The main holding frame (20) comprises four metal pieces orientated relative to each other to make a generally rectangular shape having a long axis corresponding to the axis X. One of the pieces of the main holding frame (20) perpendicular to the axis X is attached to the crankshaft (16).

In FIG. 1, the pieces of the main holding frame (20) parallel to the axis X have four semi-circular shapes (not shown) cut into the main holding frame (20) that are used to hold four capped 1000 mL glass graduated cylinders (24). Hingedly attached to one piece of the main holding frame (20) parallel to the axis X is a face holding frame (22) comprising four metal pieced orientated relative to each other to make a generally rectangular shape having a long axis corresponding to the axis X and an area equal to that of the main holding frame (20). The face holding frame (22) is hingedly attached to the main holding frame (20) such that the four capped 1000 mL glass graduated cylinders (24) can be held firmly into place in the four semi-circular shapes of the main holding frame (20), and at the same time, the four capped 1000 mL glass graduated cylinders (24) can be easily removed.

Attached to one of the pieces of the main holding frame (20) perpendicular to the axis X, opposite the piece of the main holding frame (20) attached to the crankshaft (16) is a rod (26). The rod (26) extends from the main holding frame (20) and passes through a rod mount wall (28) comprising a rod mount wall opening (29). The rod mount wall (28) is of sufficient thickness and width to support the rod (26) and sufficient height to allow the mixing apparatus (10) to rotate freely about axis X as shown in FIG. 1. The rod mount wall opening (29) is of sufficient diameter to allow the rod (26) to rotate freely about axis X.

A heavy duty liquid laundry detergent, as given below in Table 1, designed for use in horizontal axis machines, unutilized the methyl capped ACAE, from Example 3 below, resulted in 21% to 35% less suds during the mixing, or agitation, phase than did the alcohol ethoxylate tested (see Table 2) in the same heavy duty liquid laundry detergent given in Table 1 below. In addition, the foam stability of the methyl capped ACAE was much lower as seen in the post mixing results during which the solution is no longer being agitated. These benefits were observed at various levels of water hardness shown in Table 2.

Heavy Duty Liquid Laundry Detergent Surfactant System

TABLE 1

| Component | Wt % of detergent |
|---|---|
| linear alkyl benzene sulphonate | 15% |
| ACAEs of Example 4 or the AE as indicated in Table 2 | 8.4% |
| $C_{8-10}$ amido propyl dimethylamine surfactant | 1.4% |
| builders | 11.0% |
| enzymes and enzyme stabilizing agents | 3.25% |
| dispersants, chelants and optical brighteners | 2.39% |
| phase stabilizers | 19.42% |
| perfumes, dyes and other adjunct ingredients | <1% |

TABLE 2

| | | SUDS Levels during MIXING | | | | POST-MIXING | |
|---|---|---|---|---|---|---|---|
| Suds Volume (mL) for 100 mL of HDL Solution | 0 min. | 2.5 min. | 5 min. | 7.5 min. | 2.5 min. | 5 min. |
| 0 gpg | | | | | | | |
| LUTENSOL ® 24-7 (C12, 14 alcohol 7-mole ethoxylate) | 0 | 405 | 555 | 590 | 565 | 305 |
| $C_{1618}$-8.5 Methyl capped ACAE of Example 4 | 0 | 320 | 420 | 470 | 365 | 65 |
| % Reduction vs. AE | | 21% | 24% | 20% | 35% | 79% |
| 6 gpg | | | | | | | |
| LUTENSOL ® 24-7 | 0 | 280 | 280 | 265 | 75 | 10 |
| $C_{1618}$-8.5 Methyl capped ACAE of Example 4 | 0 | 180 | 200 | 180 | 10 | 10 |
| % Reduction vs. AE | | 36% | 29% | 32% | 87% | 0% |

TABLE 2-continued

|  | SUDS Levels during MIXING | | | | POST-MIXING | |
|---|---|---|---|---|---|---|
| Suds Volume (mL) for 100 mL of HDL Solution | 0 min. | 2.5 min. | 5 min. | 7.5 min. | 2.5 min. | 5 min. |
| 12 gpg | | | | | | |
| LUTENSOL ® 24-7 | 0 | 235 | 260 | 265 | 60 | 10 |
| $C_{1618}$-8.5 Methyl capped ACAE of Example 4 | 0 | 160 | 170 | 190 | 15 | 10 |
| % Reduction vs. AE | | 32% | 35% | 28% | 75% | 0% |

Moreover, under typical horizontal axis machine wash detergent concentration and water hardness conditions, the ethyl and butyl capped ACAEs of the present invention also produce fewer suds and provide reduced foam stability versus conventional alcohol ethoxylate nonionic surfactants such as the LUTENSOL® 24-7 nonionic surfactant available from BASF. This has been observed in heavy duty liquid laundry detergent formulations based on linear alkyl benzene sulfonate available from Huntsman as the core surfactant (see Table 3) as well as in experimental heavy duty liquid laundry detergents based on long mid-chain branched alkyl sulfates, discussed below, (see Table 4). From a suds reduction standpoint, the ethyl capped ACAE is preferred.

TABLE 3

Sudsing of Test compounds in HDL formulated with linear alkyl benzene sulfonate

|  | MIXING | | | | POST-MIXING | |
|---|---|---|---|---|---|---|
| Suds Volume (mL) for 100 mL of HDL Wash Solution | 0 min. | 2.5 min. | 5 min. | 7.5 min. | 2.5 min. | 5 min. |
| 12 gpg | | | | | | |
| LUTENSOL ® 24-7 (C12, 14 alcohol 7-mole ethoxylate) | 0 | 240 | 255 | 250 | 115 | 15 |
| $C_{1618}$-10.5 Ethyl capped ACAE of the present invention | 0 | 135 | 135 | 145 | 10 | 0 |
| % Reduction vs. AE | | 44% | 47% | 42% | 91% | 100% |
| $C_{1618}$-10.5 Butyl capped ACAE of Example 6 | 0 | 190 | 190 | 195 | 15 | 0 |
| % Reduction vs. AE | | 21% | 25% | 22% | 87% | 100% |

TABLE 4

Sudsing of Test compounds in HDL formulated with alkyl sulfates

|  | MIXING | | | | POST-MIXING | |
|---|---|---|---|---|---|---|
| Suds Volume (mL) for 100 mL of HDL Wash Solution | 0 min. | 2.5 min. | 5 min. | 7.5 min. | 2.5 min. | 5 min. |
| 12 gpg | | | | | | |
| LUTENSOL ® 24-7 ($C_{12,14}$ alcohol 7-mole ethoxylate) | 0 | 225 | 305 | 345 | 340 | 310 |
| $C_{1618}$-10.5 Ethyl capped ACAE of the present invention | 0 | 75 | 95 | 100 | 55 | 40 |
| % Reduction vs. AE | | 67% | 69% | 71% | 84% | 87% |
| $C_{1618}$-10.5 Butyl capped ACAE of Example 6 | 0 | 120 | 125 | 135 | 70 | 55 |
| % Reduction vs. AE | | 47% | 59% | 61% | 79% | 82% |

Even though embodiments of the ACAEs as described above are directed to ethoxylated materials. Similar structures of ACAEs could be made using other alkylene oxide moieties, such as propylene oxide moieties, both in combination with ethylene oxide and/or alone.

Formulations

One preferred aspect of the present invention relates to compositions that comprise the ACAEs of the present invention. Formulations of this aspect can be modified for use at any step in the laundry cycle, for example, as a pre-soak, as an addition to surfactant comprising compositions, as a rinse-added composition. Non-limiting examples of compositions that may comprise this aspect include: (a) from about 0.01% to about 99% by weight, of one or more ACAEs according to the present invention. Yet another embodiment of this aspect comprises, in addition to a suitable carrier, other adjunct ingredients which can enhance the performance benefits of the ACAEs or which enhance the delivery of the present ACAEs to fabric surface.

The cleaning compositions of the present invention further relate to the aspect of detersive surfactant-comprising compositions, said cleaning compositions comprising:
a) from about 0.01% to about 30% by weight of said composition of one or more ACAEs according to the present invention. Another embodiment comprises from about 0.1% to about 10% by weight of said ACAEs,
b) from about 1% to 60%, preferably 10% to 35% by weight of said composition of a surfactant system, said surfactant system comprising:
  i) from 0.01% of said composition whereas depending upon which aspect or embodiment of the present invention, the following ranges are suitable: from about 0.1% to about 100%; from about 1% to about 80%; from about 1% to about 60%, from about 1% to about 30% by weight of said surfactant system of one or more anionic surfactants, said anionic surfactants selected from the group consisting of linear alkyl benzene sulphonates, modified alkyl benzene sulphonates; linear alkyl sulfates, mid-chain branched sulfates, linear alkyleneoxy sulfates, mid-chain branched alkyleneoxy sulfates; and mixtures thereof;
  ii) optionally, from 0.01%, whereas depending upon which aspect or embodiment of the present invention, the following ranges are suitable: from about 0.1% to about 100%; from about 1% to about 80%; from about 1% to about 60%, from about 1% to about 30% by weight of said surfactant system of one or more nonionic surfactants selected from the group consisting of alcohols, alcohol ethoxylates, polyoxyalkylene alkylamides, and mixtures thereof; and
c) the balance carriers and other adjunct ingredients.

Surfactant System

The cleaning compositions of the present invention comprise a surfactant system. The surfactant systems of the present invention may comprise any type of detersive surfactant, non-limiting examples of which include one or more mid-chain branched alkyl sulfate surfactants, one or more mid-chain branched alkyl alkoxy sulfate surfactants, one or more mid-chain branched aryl sulfonate surfactants, one or more non mid-chain branched sulphonates, sulphates, cationic surfactants, zwitterionic surfactants, ampholytic surfactants, and mixtures thereof.

The total amount of surfactant present in the compositions of the present invention is from about 0.01% by weight, preferably from about 0.1% more preferably from about 1% to about 60%, preferably to about 30% by weight, of said composition.

Nonlimiting examples of surfactants useful herein include:
a) $C_1$-$C_{18}$ alkyl benzene sulfonates (LAS);
b) $C_6$-$C_{18}$ mid-chain branched aryl sulfonates (BLAS);

c) $C_{10}$-$C_{20}$ primary, α or ω-branched, and random alkyl sulfates (AS);

d) $C_{14}$-$C_{20}$ mid-chain branched alkyl sulfates (BAS);

e) $C_{10}$-$C_{18}$ secondary (2,3) alkyl sulfates as described in U.S. Pat. No. 3,234,258 Morris, issued Feb. 8, 1966; U.S. Pat. No. 5,075,041 Lutz, issued Dec. 24, 1991; U.S. Pat. No. 5,349,101 Lutz et al., issued Sep. 20, 1994; and U.S. Pat. No. 5,389,277 Prieto, issued Feb. 14, 1995;

f) $C_{10}$-$C_{18}$ alkyl alkoxy sulfates ($AE_xS$) wherein preferably x is from 1-7;

g) $C_{14}$-$C_{20}$ mid-chain branched alkyl alkoxy sulfates ($BAE_xS$), where x is from 1 to 50;

h) $C_{10}$-$C_{18}$ alkyl alkoxy carboxylates preferably comprising 1-5 ethoxy units;

i) $C_{12}$-$C_{18}$ alkyl ethoxylates, $C_6$-$C_{12}$ alkyl phenol alkoxylates wherein the alkoxylate units are a mixture of ethyleneoxy and propyleneoxy units, $C_{12}$-$C_{18}$ alcohol and $C_6$-$C_{12}$ alkyl phenol condensates with ethylene oxide/propylene oxide block polymers inter alia PLURONIC® ex BASF which are disclosed in U.S. Pat. No. 3,929,678 Laughlin et al., issued Dec. 30, 1975;

j) $C_{14}$-$C_{22}$ mid-chain branched alkyl alkoxylates, $BAE_x$, wherein preferably x is from 1 to 50;

k) Alkylpolysaccharides as disclosed in U.S. Pat. No. 4,565,647 Llenado, issued Jan. 26, 1986;

l) Polyhydroxy fatty acid amides having the formula (IV):

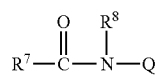

(IV)

wherein $R^7$ of formula (IV) is $C_5$-$C_{31}$ alkyl; $R^8$ of formula (IV) is selected from the group consisting of hydrogen, $C_1$-$C_4$ alkyl, $C_1$-$C_4$ hydroxyalkyl, Q of formula (IV) is a polyhydroxyalkyl moiety having a linear alkyl chain with at least 3 hydroxyls directly connected to the chain, or an alkoxylated derivative thereof; preferred alkoxy is ethoxy or propoxy, and mixtures thereof; preferred Q is derived from a reducing sugar in a reductive amination reaction, more preferably Q is a glycityl moiety; Q is more preferably selected from the group consisting of —$CH_2(CHOH)_nCH_2OH$, —$CH(CH_2OH)(CHOH)_{n-1}CH_2OH$, $CH_2(CHOH)_2(CHOR')(CHOH)CH_2OH$, and alkoxylated derivatives thereof, wherein n is an integer from 3 to 5, inclusive, and R' is hydrogen or a cyclic or aliphatic monosaccharide, which are described in U.S. Pat. No. 5,489,393 Connor et al., issued Feb. 6, 1996; and U.S. Pat. No. 545,982 Murch et al., issued Oct. 3, 1995.

A non-limiting example of a nonionic surfactant suitable for use in the present invention has the formula (V):

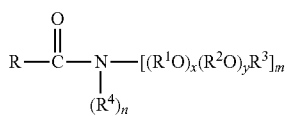

(V)

wherein R of formula (V) is $C_7$-$C_{21}$ linear alkyl, $C_7$-$C_{21}$ branched alkyl, $C_7$-$C_{21}$ linear alkenyl, $C_7$-$C_{21}$ branched alkenyl, and mixtures thereof.

$R^1$ of formula (V) is ethylene; $R^2$ of formula (V) is $C_3$-$C_4$ linear alkyl, $C_3$-$C_4$ branched alkyl, and mixtures thereof; preferably $R^2$ is 1,2-propylene. Nonionic surfactants which comprise a mixture of $R^1$ and $R^2$ units preferably comprise from about 4 to about 12 ethylene units in combination with from about 1 to about 4 1,2-propylene units. The units may be alternating, or grouped together in any combination suitable to the formulator. Preferably the ratio of $R^1$ units to $R^2$ units is from about 4:1 to about 8:1. Preferably $R^2$ units are attached to the nitrogen atom followed by the balance of the chain comprising from 4 to 8 ethylene units.

$R^3$ of formula (V) is hydrogen, $C_1$-$C_4$ linear alkyl, $C_3$-$C_4$ branched alkyl, and mixtures thereof; preferably hydrogen or methyl, more preferably hydrogen.

$R^4$ of formula (V) is hydrogen, $C_1$-$C_4$ linear alkyl, $C_3$-$C_4$ branched alkyl, and mixtures thereof; preferably hydrogen. When the index m of formula (V) is equal to 2 the index n of formula (V) must be equal to 0 and the $R^4$ unit is absent and is instead replaced by a —$[(R^1O)_x(R^2O)_yR^3]$ unit, wherein $R^1$, $R^2$, and $R^3$ are as defined above in formula (V), and x and y are as defined here in below for formula (V).

The index m of formula (V) is 1 or 2, the index n of formula (V) is 0 or 1, provided that when m is equal to 1, n is equal to 1; and when m is 2 n is 0; preferably m is equal to 1 and n is equal to 1, resulting in one —$[(R^1O)_x(R^2O)_yR^3]$ unit and $R^4$ being present on the nitrogen. The index x of formula (V) is from 0 to about 50, preferably from about 3 to about 25, more preferably from about 3 to about 10. The index y of formula (V) is from 0 to about 10, preferably 0, however when the index y is not equal to 0, y is from 1 to about 4. Preferably all of the alkyleneoxy units are ethyleneoxy units. Those skilled in the art of ethoxylated polyoxyalkylene alkyl amide surface active agents will recognized that the values for the indices x and y are average values and the true values may range over several values depending upon the process used to alkoxylate the amides.

The mid-chain branched alkyl sulfate surfactants of the present invention have the formula (VI):

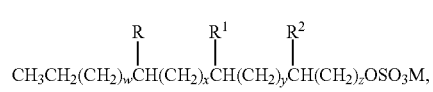

(VI)

the alkyl alkoxy sulfates have the formula (VII):

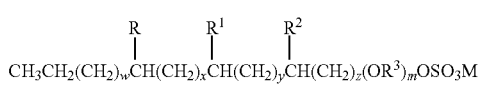

(VII)

the alkyl alkoxylates have the formula (VIII):

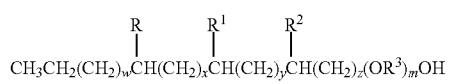

(VIII)

wherein R, $R^1$, and $R^2$ of formulas (VI)-(VIII) are each independently hydrogen, $C_1$-$C_3$ alkyl, and mixtures thereof; provided at least one of R, $R^1$, and $R^2$ is not hydrogen; preferably R, $R^1$, and $R^2$ are methyl; preferably one of R, $R^1$, and $R^2$ is methyl and the other units are hydrogen. The total number of carbon atoms in the mid-chain branched alkyl sulfate and alkyl alkoxy sulfate surfactants is from 14 to 20; the index w of formulas (VI)-(VIII) is an integer from 0 to 13; x of formulas (VI)-(VIII) is an integer from 0 to 13; y of formulas (VI)-(VIII) is an integer from 0 to 13; z of formulas (VI)-(VIII) is an integer of at least 1; provided w+x+y+z is from 8 to 14 and the total number of carbon atoms in a surfactant is from 14 to 20; $R^3$ of formulas (VII) and (VIII) is $C_1$-$C_4$ linear or branched alkylene, preferably ethylene, 1,2-propylene, 1,3-propylene, 1,2-butylene, 1,4-butylene, and mixtures thereof. However, a preferred embodiment of the present invention comprises from 1 to 3 units wherein $R^3$ is 1,2-propylene, 1,3-propylene, or mixtures thereof followed by the balance of the $R^3$ units comprising ethylene units. Another preferred embodiment comprises $R^3$ units which are randomly ethylene and 1,2-propylene units. The average value of the index m of formulas (VII) and (VIII) is at least about 0.01. When the index m has low values, the surfactant system comprises mostly alkyl sulfates with a small amount of alkyl alkoxy sulfate surfactant. Some tertiary carbon atoms may be present in the alkyl chain, however, this embodiment is not desired.

M of formulas (VI) and (VII) denotes a cation, preferably hydrogen, a water soluble cation, and mixtures thereof. Non-limiting examples of water soluble cations include sodium, potassium, lithium, ammonium, alkyl ammonium, and mixtures thereof.

Adjunct Ingredients

The following are non-limiting examples of adjunct ingredients useful in the cleaning compositions of the present invention, The precise nature of these additional components, and levels of incorporation thereof, will depend on the physical form of the composition and the nature of the cleaning operation for which it is to be used. Suitable adjunct materials include, but are not limited to, surfactants, builders, chelating agents, dye transfer inhibiting agents, dispersants, enzymes, and enzyme stabilizers, catalytic metal complexes, polymeric dispersing agents, clay soil removal/anti-redeposition agents, optical brighteners, suds suppressors, dyes, perfumes, structure elasticizing agents, fabric softeners, carriers, hydrotropes, phase stabilizers, processing aids and/or pigments. Other adjuncts well known in the art are also suitable for use herein.

Builders

The cleaning compositions of the present invention preferably comprise one or more builders or builder systems. When present, the cleaning compositions will typically comprise at least about 1% by weight of the cleaning composition of builder, preferably from 5% to about 80% by weight of the cleaning composition of a builder; more preferably from about 10% to about 30% by weight of the cleaning composition of a builder.

Inorganic or P-containing builders include, but are not limited to, the alkali metal, ammonium and alkanolammonium salts of polyphosphates (exemplified by the tripolyphosphates, pyrophosphates, and glassy polymeric metaphosphates), phosphonates, phytic acid, silicates, carbonates (including bicarbonates and sesquicarbonates), sulphates, and aluminosilicates. Examples of silicate builders are the alkali metal silicates, examples of which include those having a $SiO_2$:$Na_2O$ ratio in the range 1.6:1 to 3.2:1 and layered silicates as described in U.S. Pat. No. 4,664,839 Rieck, issued May 12, 1987 which include NaSKS-6® ex Hoechst. Others include NaSKS-5®, NaSKS-7®, and NaSKS-11® also ex Hoechst. Examples of carbonate builders are the alkaline earth and alkali metal carbonates as disclosed in German Patent Application No. 2,321,001 published on Nov. 15, 1973. Aluminosilicate builders include those having the empirical formula: $[M_z(zAlO_2)_y]xH_2O$, wherein z and y are integers of at least 6, the molar ratio of z to y is in the range from 1.0 to about 0.5, and x is an integer from about 15 to about 264, known as Zeolite A, Zeolite P (B), Zeolite MAP and Zeolite X. In one embodiment, the crystalline aluminosilicate ion exchange material has the formula: $Na_{12}[(AlO_{12})_{12}(SiO_2)_{12}]xH_2O$, wherein x is from about 20 to about 30, especially about 27. This material is known as Zeolite A. Preferably, the aluminosilicate has a particle size of about 0.1-10 microns in diameter.

Included among the polycarboxylate builders are those disclosed in U.S. Pat. No. 3,128,287 Berg, issued Apr. 7, 1964, and U.S. Pat. No. 3,635,830 Lamberti et al., issued Jan. 18, 1972; U.S. Pat. No. 4,663,071 Bush et al., issued May 5, 1987; U.S. Pat. No. 3,923,679 Rapko, issued Dec. 2, 1975; U.S. Pat. No. 4,158,635 Crutchfield et al., issued Jun. 19, 1979; U.S. Pat. No. 4,120,874 Crutchfield et al., issued Oct. 17, 1978; and U.S. Pat. No. 4,102,903 Crutchfield et al., issued Jul. 25, 1978. Other useful detergency builders include the ether hydroxypolycarboxylates, copolymers of maleic anhydride with ethylene or vinyl methyl ester, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders of particular importance for heavy-duty liquid detergent formulations due to their availability from renewable resources and their biodegradability. Citrates can also be used in granular compositions, especially in combination with zeolite and/or layered silicate builders. Oxydisuccinates are also especially useful in such compositions and combinations.

Other suitable builders are disclosed in U.S. Pat. No. 4,566,984, Bush, issued Jan. 28, 1986; U.S. Pat. No. 4,144,226, Crutchfield et al., issued Mar. 13, 1979 and in U.S. Pat. No. 3,308,067, Diehl, issued Mar. 7, 1967 and U.S. Pat. No. 3,723,322.

Fatty acids, e.g., $C_{12}$-$C_{18}$ monocarboxylic acids, can also be incorporated into the cleaning compositions alone, or in combination with the aforesaid builders. In embodiments wherein phosphorus-based builders are used the various alkali metal phosphates, inter alia, sodium tripolyphosphates, sodium pyrophosphate and sodium orthophosphate can be used. Phosphonate builders such as ethane-1-hydroxy-1,1-diphosphonate and other known phosphonates as described in U.S. Pat. Nos. 3,159,581; 3,213,030; 3,422,021; 3,400,148 and 3,422,137.

Dispersants

The cleaning compositions of the present invention may comprise from about 0.01% to about 10% by weight of the cleaning composition of one or more polyalkyleneimine dispersants as described in U.S. Pat. No. 4,597,898 Vander Meer, issued Jul. 1, 1986; European Patent Application 111,965 Oh and Gosselink, published Jun. 27, 1984; European Patent Application 111,984 Gosselink, published Jun. 27, 1984; European Patent Application 112,592 Gosselink, published Jul. 4, 1984; U.S. Pat. No. 4,548,744 Connor, issued Oct. 22, 1985; and U.S. Pat. No. 5,565,145 Watson et al., issued Oct. 15, 1996. However, any suitable clay/soil dispersant or anti-redeposition agent can be used in the cleaning compositions of the present invention.

The cleaning compositions of the present invention may comprise from about 0.01% to about 10% by weight of the cleaning composition of one or more polymeric polycarboxylates and polyethylene glycols. For example, polymeric polycarboxylates and polyethylene glycols derived from acrylic acid, maleic acid (or maleic anhydride), fumaric acid, itaconic acid, aconitic acid, mesaconic acid, citraconic acid and methylenemalonic acid. These monomers can be used alone, in combination with each other monomers or in combination of units such as vinylmethyl ester, styrene, ethylene, and the like, provided that such segments do not constitute more than about 40% by weight of said polymer.

One embodiment of the present invention comprises from about 0.01% to about 10% by weight of the cleaning composition of polymeric polycarboxylates derived from acrylic acid having an average weight molecular weight of from about 2,000 to about 10,000. In another embodiment of the present invention, the cleaning composition comprises polymeric polycarboxylates derived from acrylic acid having an average weight molecular weight of from about 4,000 to about 7,000 or from about 4,000 to about 5,000. Polyacrylates of this type are disclosed in U.S. Pat. No. 3,308,067 Diehl, issued Mar. 7, 1967.

In addition, acrylic/maleic-based copolymers having average weight molecular weights ranging from about 2,000 to about 100,000 are useful in the present invention. However, depending upon the embodiment, molecular weight ranges may include from about 5,000 to about 75,000, and from about 7,000, to about 65,000. The ratio of acrylate to maleate segments in such copolymers will generally range from about 30:1 to about 1:1, however, about 10:1 to about 2:1 is also useful as a further embodiment. Acrylate/maleate copolymers described in European Patent Application No. 66915, published Dec. 15, 1982, and EP 193,360, published Sep. 3, 1986.

A further embodiment of the present invention comprises from about 0.01% to about 10% by weight of the cleaning composition of polyethylene glycol (PEG) having an average weight molecular weight range of from about 500 to about 100,000; preferably from about 1,000 to about 50,000; and more preferably from about 1,500 to about 10,000.

Enzymes

The cleaning composition can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and known amylases, or mixtures thereof. A preferred combination is a cleaning composition having a cocktail of conventional applicable enzymes like protease, lipase, cutinase and/or cellulase in conjunction with the amylase of the present invention.

Enzyme Stabilizers

Enzymes for use in cleaning composition can be stabilized by various techniques. The enzymes employed herein can be stabilized by the presence of water-soluble sources of calcium and/or magnesium ions in the finished compositions that provide such ions to the enzymes.

Chelating Agents

The cleaning compositions herein may also optionally contain one or more iron and/or manganese chelating agents. Such chelating agents can be selected from the group consisting of amino carboxylates, amino phosphonates, polyfunctionally-substituted aromatic chelating agents and mixtures therein, all as hereinafter defined. Amino carboxylates useful as optional chelating agents include ethylenediaminetetracetates, N-hydroxyethylethylenediaminetriacetates, nitrilotriacetates, ethylenediamine tetraproprionates, triethylenetetraaminehexacetates, diethylenetriaminepentaacetates, and ethanoldiglycines, alkali metal, ammonium, and substituted ammonium salts therein and mixtures therein. Amino phosphonates are also suitable for use as chelating agents in the compositions of the invention when at lease low levels of total phosphorus are permitted in detergent compositions, and include ethylenediaminetetrakis(methylenephosphonates) as DEQUEST®. Preferred, these amino phosphonates to not contain alkyl or alkenyl groups with more than about 6 carbon atoms. Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene. A preferred biodegradable chelator for use herein is ethylenediamine disuccinate ("EDDS"), especially the [S,S] isomer as described in U.S. Pat. No. 4,704,233, Nov. 3, 1987, to Hartman and Perkins. If utilized, these chelating agents will generally comprise from about 0.1% to about 10% by weight of the cleaning composition s herein. More preferably, if utilized, the chelating agents will comprise from about 0.1% to about 3.0% by weight of such compositions.

Brightener

Any optical brighteners or other brightening or whitening agents known in the art can be incorporated at levels typically from about 0.01% to about 1.2%, by weight, into the cleaning compositions herein. Commercial optical brighteners which may be useful in the present invention can be classified into subgroups, which include, but are not necessarily limited to, derivatives of stilbene, pyrazoline, coumarin, carboxylic acid, methinecyanines, dibenzothiophene-5,5-dioxide, azoles, 5- and 6-membered-ring heterocycles, and other miscellaneous agents. Specific examples of optical brighteners that are useful in the present compositions are those identified in U.S. Pat. No. 4,790,856, issued to Wixon on Dec. 13, 1988. See also U.S. Pat. No. 3,646,015, issued Feb. 29, 1972 to Hamilton.

Phase Stabilizers

The cleaning composition according to the present invention may optionally comprise one or more phase stabilizers. If utilized, phase stabilizers will generally comprise from about 0.01% to about 50% by weight of the cleaning composition. Suitable phase stabilizers for use in the present invention include, but are not limited to solvents such as ethanol, 1,2 propanediol and monoethanol amine.

Soil Release Agents

The cleaning compositions according to the present invention may optionally comprise one or more soil release agents. If utilized, soil release agents will generally comprise from about 0.01% to about 10% by weight of the cleaning composition.

Soil release agents suitable for use in the present invention are described in U.S. Pat. No. 5,843,878 Gosselink et al., issued Dec. 1, 1998; U.S. Pat. No. 5,834,412 Rohrbaugh et al., issued Nov. 10, 1998; U.S. Pat. No. 5,728,671 Rohrbaugh et al., issued Mar. 17, 1998; U.S. Pat. No. 5,691,298 Gosselink et al., issued Nov. 25, 1997; U.S. Pat. No. 5,599,782 Pan et al., issued Feb. 4, 1997; U.S. Pat. No. 5,415,807 Gosselink et al., issued May 16, 1995; U.S. Pat. No. 5,182,043 Morrall et al., issued Jan. 26, 1993; U.S. Pat. No. 4,956,447 Gosselink et al., issued Sep. 11, 1990; U.S. Pat. No. 4,976,879 Maldonado et al., issued Dec. 11, 1990; U.S. Pat. No. 4,968,451 Scheibel et al., issued Nov. 6, 1990; U.S. Pat. No. 4,925,577 Borcher, Sr. et al., issued May 15, 1990; U.S. Pat. No. 4,861,512 Gosselink, issued Aug. 29, 1989; U.S. Pat. No.

4,877,896 Maldonado et al., issued Oct. 31, 1989; U.S. Pat. No. 4,702,857 Gosselink et al., issued Oct. 27, 1987; U.S. Pat. No. 4,711,730 Gosselink et al., issued Dec. 8, 1987; U.S. Pat. No. 4,721,580 Gosselink issued Jan. 26, 1988; U.S. Pat. No. 4,000,093 Nicol et al., issued Dec. 28, 1976; U.S. Pat. No. 3,959,230 Hayes, issued May 25, 1976; U.S. Pat. No. 3,893,929 Basadur, issued Jul. 8, 1975; and European Patent Application 0 219 048, published Apr. 22, 1987 by Kud et al.

Further suitable soil release agents are described in U.S. Pat. No. 4,201,824 Voilland et al.; U.S. Pat. No. 4,240,918 Lagasse et al.; U.S. Pat. No. 4,525,524 Tung et al.; U.S. Pat. No. 4,579,681 Ruppert et al.; U.S. Pat. No. 4,220,918; U.S. Pat. No. 4,787,989; EP 279,134 A, 1988 to Rhone-Poulenc Chemie; EP 457,205 A to BASF (1991); and DE 2,335,044 to Unilever N.V., 1974.

PREPARATIVE EXAMPLES

Example 1

Figure 2:
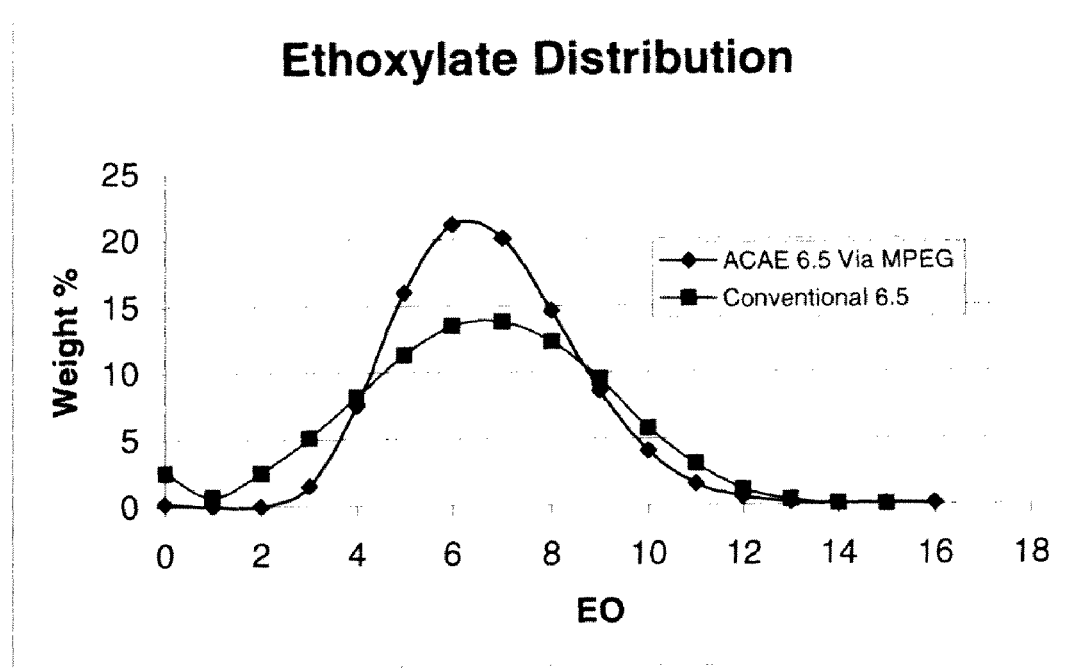
FIG. 2 is the ethoxylate distribution of the ACAEs of the present invention.

Synthesis of $C_{16}$-$C_{18}$ ACAE from MPEG 6.5 Being Substantially Free of $R_1E_1$ and $R_1E_2$ In a dried 1-liter 3 neck round bottom flask fitted with a gas inlet, mechanical stirrer, and a y-tube fitted with a thermometer and a gas outlet, triethylene glycol monomethyl ether (126 g, 0.77 moles) and sodium (1.01 g, 0.044 moles) is heated under a nitrogen atmosphere to 120° C. with stirring to form the alkoxide. Ethylene oxide (119 g, 2.70 moles) is introduced as a gas at rate of 0.70 g/minute to give the poly(ethylene glycol)monomethyl ether with an average ethoxylation of 6.5. To this is added $C_{16-18}$ fatty acid methyl ester (240 g, 0.85 moles) and sodium methoxide (2.51 g, 0.046 moles) then heated to 100° C. while reducing the pressure to about 0.267 kPa (2 mm Hg) over a period of 5 hours in Kugelrohr (bulb to bulb) distillation apparatus. The reaction is completed and excess starting $C_{16-18}$ fatty acid methyl ester is removed by increasing temperature and vacuum to 180° C. and about 0.033 kPa (0.25 mm Hg). The cooled reaction mixture is diluted with 500 ml of anhydrous diethyl ether, filtered and stirred over AMBERLYST 15®. Resultant suspension is filtered through CELITE® and the ether is removed using a roto-vap under reduced pressure via water aspirator to give an ACAE with the resultant ethoxylate distribution as depicted in FIG. 2.

Example 2

Ethoxylation of Triethylene Glycol Monomethyl Ether

In a dried 1-liter 3 neck round bottom flask fitted with a gas inlet, mechanical stirrer, and a y-tube fitted with a thermometer and a gas outlet, triethylene glycol monomethyl ether (202 g, 1.23 moles) and sodium (1.56 g, 0.068 moles) is heated under a nitrogen atmosphere to 120° C. with stirring to form the alkoxide ethylene oxide (298 g, 6.77 moles) is introduced as a gas at rate of 0.70 g/minute. Mixture is neutralized with concentrated HCl after diluting with 500 mL of methanol. Methanol is removed using a roto-vap under reduced pressure via water aspirator. Resultant cloudy yellow oil is dissolved in 500 mL anhydrous ether and dried over 20 g of sodium sulfate, filtered through Celite and the ether is removed using a roto-vap under reduced pressure via water aspirator to give the poly(ethylene glycol)monomethyl ether with an average ethoxylation of 8.5.

Example 3

Synthesis of $C_{16}$-$C_{18}$ ACAE from MPEG 8.5 Being Substantially Free of $R_1E_1$ and $R_1E_2$ In a dried 1-liter round bottom flask $C_{16-18}$ fatty acid methyl ester (76 g, 0.27 moles), MPEG 8.5 from triethylene glycol monomethyl ether according to Example 1 (101 g, 0.25 moles) and sodium methoxide (1.1 g, 0.02 moles) is heated to 100° C. while reducing the pressure to about 0.267 kPa (2 mm Hg) over a period of 5 hours in Kugelrohr (bulb to bulb) distillation apparatus. The reaction is completed and excess starting $C_{16-18}$ fatty acid methyl ester is removed by increasing temperature and vacuum to 180° C. and about 0.033 kPa (0.25 mm Hg). The cooled reaction mixture is diluted with 250 ml of anhydrous diethyl ether, filtered and stirred over AMBERLYST 15®. Resultant suspension is filtered through CELITE® and the ether is removed using a roto-vap under reduced pressure via water aspirator to give an ACAE with the formula (I):

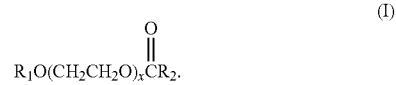

(I) wherein $R_1$ is methyl, $R_2$ is $C_{16}$-$C_{18}$ and x is 8.5.

Example 4

Synthesis of $C_{16}$-$C_{18}$ ACAE from MPEG 7.2 [$R_1E_1$ and $R_1E_2$ Post Synthesis Removal]

In a dried 1-liter round bottom flask $C_{16-18}$ fatty acid methyl ester (78 g, 0.28 moles), MPEG 7.2 (88 g, 0.25 moles) and sodium methoxide (1.1 g, 0.02 moles) is heated to 100° C. while reducing the pressure to about 2.67 kPa (2 mm Hg) over a period of 5 hours in Kugelrohr (bulb to bulb) distillation apparatus. Reaction is completed, excess starting $C_{16-18}$ fatty acid methyl ester and $R_1E_1$ and $R_1E_2$ are removed by increasing temperature and vacuum to 180° C. and about 0.033 kPa (0.25 mm Hg) then further increasing temperature to 210° C. and about 6.67 Pa (0.05 mm Hg). The cooled reaction mixture is diluted with 250 ml of anhydrous diethyl ether, filtered and stirred over AMBERLYST 15®. The resultant suspension is filtered through CELITE® and the ether is removed using a roto-vap under reduced pressure via water aspirator to give an ACAE with the formula (I):

(I) wherein $R_1$ is methyl, $R_2$ is $C_{16}$-$C_{18}$ and x is 7.2.

Example 5

Synthesis $C_{16}$-$C_{18}$ACAE from Stripped MPEG 7.2

In a dried 1-liter round bottom flask MPEG 7.2 (88 g, 0.25 moles) is heated to 100° C. at a reduced pressure to about 2.67 kPa (2 mm Hg) to remove ethylene glycol alkyl ether ($R_1O(CH_2CH_2O)H$) and diethylene glycol alkyl ether ($R_1O(CH_2CH_2O)_2H$). To this stripped MPEG is added $C_{16-18}$ fatty acid methyl ester (78 g, 0.28 moles) and sodium methoxide (1.1 g, 0.02 moles) then heated to 100° C. while reducing the pressure to about 2.67 kPa (2 mm Hg) over a period of 5 hours in Kugelrohr (bulb to bulb) distillation apparatus. Reaction is completed and excess starting $C_{16-18}$ fatty acid methyl ester is removed by increasing temperature and vacuum to 180° C. and about 0.033 kPa (0.25 mm Hg). The cooled reaction mixture is diluted with 250 ml of anhydrous diethyl ether, filtered and stirred over AMBERLYST 15®. The resultant suspension is filtered through CELITE® and the ether is removed using a roto-vap under reduced pressure via water aspirator to give an ACAE with the formula (I):

$$R_1O(CH_2CH_2O)_xCR_2 \overset{O}{\underset{\|}{}} \tag{I}$$

(I) wherein $R_1$ is methyl, $R_2$ is $C_{16}$-$C_{18}$ and x is 7.2.

Example 6

Synthesis of $C_{16}$-$C_{18}$ ACAE from Polyethylene Glycol Monobutyl Ether 10.5 Containing Substantially No $R_1E_1$-$R_1E_2$ In a dried 1-liter round bottom flask $C_{16-18}$ fatty acid methyl ester (61 g, 0.22 mols), BPEG 10.5, free of ethylene glycol butyl ether and diethylene glycol butyl ether, (94 g, 0.17 mols) and sodium methoxide (0.94 g, 0.017 mols) is heated to 100° C. while reducing the pressure to about 2.67 kPa (2 mm Hg) over a period of 5 hours in Kugelrohr (bulb to bulb) distillation apparatus. Reaction is completed and excess starting $C_{16-18}$ fatty acid methyl ester is removed by increasing temperature and vacuum to 180° C. and about 0.033 kPa (0.25 mm Hg). The cooled reaction mixture is diluted with 250 ml of anhydrous diethyl ether, filtered and stirred over AMBERLYST 15®. The ensuing suspension is filtered through CELITE® and the ether is removed using a roto-vap under reduced pressure via water aspirator to give the ethoxylated methyl ester.

What is claimed is:

1. A composition comprising a mixture of compounds having the formula (I):

$$R_1O(CH_2CH_2O)_xCR_2 \overset{O}{\underset{\|}{}} \tag{I}$$

wherein $R_1$ is a $C_1$ to $C_4$ hydrocarbon, linear or branched, and mixtures thereof, $R_2$ is $C_7$ to $C_{22}$ hydrocarbon, linear or branched, and mixtures thereof; and x is greater than 3 and is in the average range of 6.5 to 8.5; said composition being free of ethylene glycol monoalkoxy monoester having formula (I) wherein x is equal to 1 and diethylene glycol monoalkoxy monoester having formula (I) wherein x is equal to 2.

* * * * *